United States Patent [19]
Leighton

[11] Patent Number: 6,043,079
[45] Date of Patent: Mar. 28, 2000

[54] CELL GROWTH APPARATUS FOR HISTOPHYSIOLOGIC CULTURE

[75] Inventor: Joseph Leighton, 2324 Lakeshore Ave., #2, Oakland, Calif. 94606

[73] Assignee: Joseph Leighton, Oakland, Calif.

[21] Appl. No.: 08/646,171

[22] Filed: May 7, 1996

[51] Int. Cl.[7] .................................................. A01N 1/02
[52] U.S. Cl. .................................... 435/283.1; 435/289.1; 435/395; 435/398; 435/401
[58] Field of Search .............................. 435/283.1, 289.1, 435/401, 395, 398

[56] References Cited

PUBLICATIONS

Graham, C.H. et al., "Rapid Acquisition of Multicellular Drug Resistance After a Single Exposure of Mammary Tumor Cells to Antitumor Alkylating Agents", *J. of the Natl. Cancer Inst.*, vol. 86, No. 3, pp. 975–982 (1994).

Leighton, J., "Exploring Process of Organization of Normal and Neoplastic Epithelial Tissues in Gradient Culture", *J. of Cell. Biochem.*, vol. 56, No. 29, pp. 29–36 (1994).

Leighton, J., "Radial Histophysiologic Gradient Culture Chamber: Rationale and Preparation", *In Vitro Cell. Dev. Biol.*, vol. 27 A, pp. 786–790 (1991).

Leighton, J., "Structural Biology of Epithelial Tissue in Histophysiologic Gradient Culture", *In Vitro Cell. Dev. Biol.*, vol. 28A, pp. 482–492 (1992).

*Primary Examiner*—Leon B. Lankford, Jr.
*Attorney, Agent, or Firm*—Morrison & Foerster LLP

[57] ABSTRACT

The present invention provides an apparatus and methods for incubating cells which rely on the use of a semipermeable membrane placed between two planar members, at least one planar member having an aperture.

12 Claims, 4 Drawing Sheets

FIG. 1
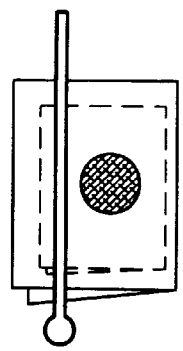
FIG. 2A
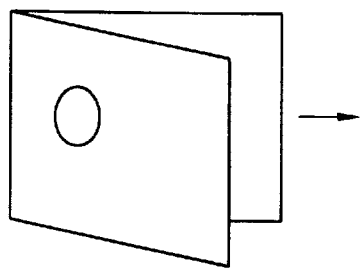
FIG. 2B
FIG. 2C
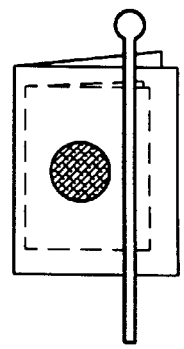
FIG. 2D
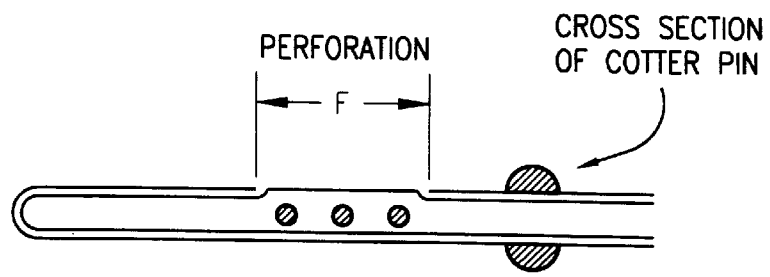
PERFORATION
F
CROSS SECTION OF COTTER PIN

FIG. 3A
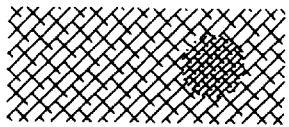
FIG. 3B
FIG. 3C
FIG. 3D
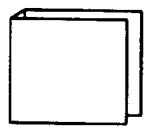  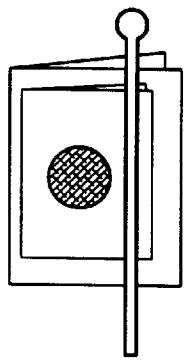 
FIG. 3E
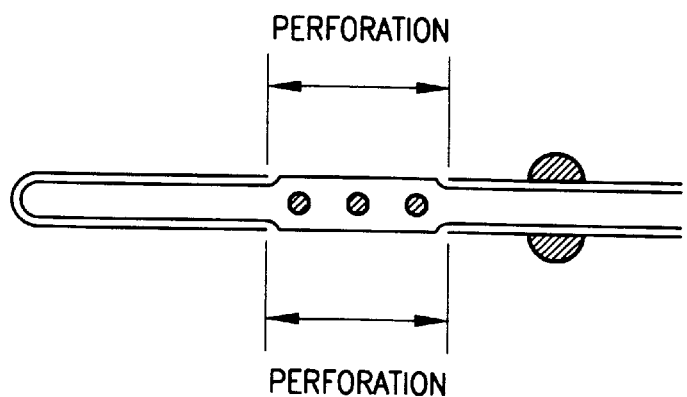

FIG. 4A
FIG. 4B
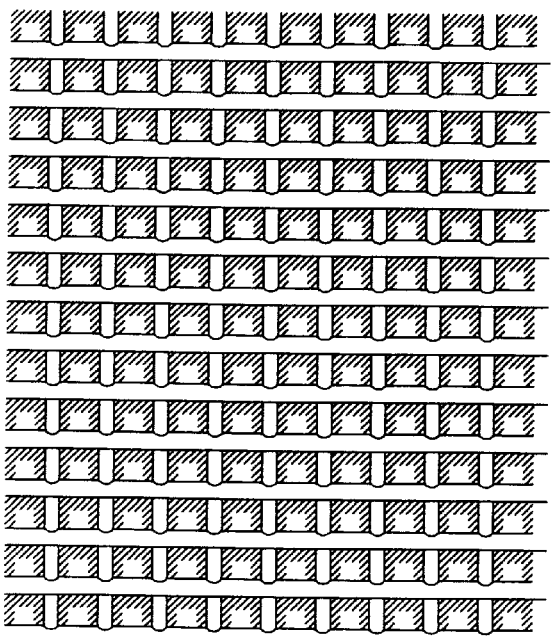
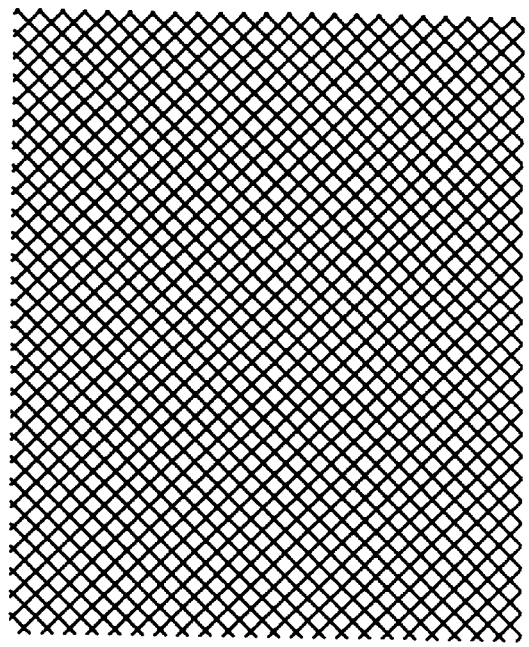
FIG. 5
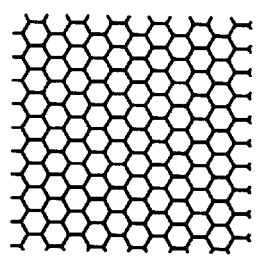

CELL GROWTH APPARATUS FOR HISTOPHYSIOLOGIC CULTURE

TECHNICAL FIELD

The invention relates to the field of cell culture apparatus and to methods of culturing cell lines or tissue fragments. More specifically, it concerns a conveniently constructed chamber for adherent cell cultures that mimics natural conditions for cellular growth and tissue structure.

BACKGROUND ART

Many types of animal cells attach to and proliferate on various types of permeable surfaces such as collagen membranes. Attached to a thin transparent membrane, masses of cells can grow in a histophysiologic way, obtaining the required metabolites and disposing of products of metabolism by diffusion across the permeable supporting membrane. Under these conditions of culture, both columnar and stratified epithelial tissues are polarized. Initiation of cellular renewal in the tissue takes place near the plane of attachment to the membrane, and all metabolic exchange with the medium outside the pouch occurs across the membrane. These conditions are "histophysiologic". Histophysiologic gradient cultures mimic the situation in nature where attachment and exchange of metabolites occur at the stromal-parenchymal interface. The apparatus of the present invention provides a setting for cell growth similar to that found in nature.

In the history of studying tumor growth by transplantation to animals, a number of sites, some as chambers, have been employed. Examples are the anterior chamber of the guinea pig and the frog eye, the hamster cheek pouch, and subcutaneous sites when an injection of air and inoculum establish a pouch. Inocula of tumors in each of these examples are in an extremely complex setting, since in each case the biology of the host is poorly understood. The vitelline membrane enclosing the yolk of the chick egg has been used as a wrapping, a pouch, for the growth in culture of human gastrointestinal carcinomas.

Considerable societal pressure exists to reduce the use of laboratory animals in toxicology. There are two important questions to consider in such testing, the presence and degree of toxic effect and the potential for reversal of the toxic effect. Tests where death of tissue is the end point do not provide information on reversibility or recovery. If an organoid association of cells displays as its first response to a toxic material a consistent disruption of architectural organization, such a disruption may or may not be reversed by the prompt removal of the toxic material. Models of the type described here, using test cells such as human cell lines or primary isolates of human amnion or epidermis, may provide useful alternatives to laboratory animals.

The motivation to develop kits for preparation of histophysiologic gradient cultures are two-fold. First, there is a growing appreciation today in cell biology research of the physiologic importance of cells in organoid tissue arrangements. The configuration of cells as tissue is significant in areas as diverse as hepatic function, and physiologic response of mammary carcinoma cells to therapy. A recent study even suggests that the spatial relationship between cancer cells appears to determine the rapid acquisition of multicellular drug resistance to alkylating agents (Graham, C. H., et al., *J.N.C.I.* (1994) 86:975–982).

Second, the development of a histophysiologic gradient culture system will accelerate the acquisition of fundamental information and the study of problems of clinical oncology. Various systems have been devised for culturing adherent cells supported on permeable membranes. A review of some of these methods is found in Leighton, *J Cell Biochem* (1994) 56:29–36. These methods include collagen-coated cellulose sponges, encapsulation into microcapsules, and, less conveniently, animal-derived sites such as the anterior chamber of guinea pig and frog eye, the hamster cheek pouch. Use of animal-derived environments has obvious disadvantages, and the various methods described in the prior art lack convenience and simplicity of construction.

SUMMARY OF THE INVENTION

The present invention provides an apparatus for culturing tissues or cells that can be adapted for inclusion in a kit packaged for routine use. The apparatus is easily manipulated and inexpensive to manufacture.

Specifically, the invention is directed to an apparatus for use in culturing tissues or cells. There are two primary configurations of the present apparatus. In one configuration, a unilaminar culture apparatus, the apparatus comprises two planar members, preferably of clear plastic, one of which contains an aperture in a portion of its area. In the second configuration, a bilaminar culture apparatus, the second planar member will have a corresponding aperture.

Disposed between the two planar members in both configurations is a pouch constructed of a permeable membrane that is permeable to nutrients and waste products but impermeable to cells. The membrane can have smooth surfaces. However, it is preferred that at least one of the surfaces of the membrane that faces the cavity formed within the pouch has a series of ridges that forms a waffle-shaped lattice on the surface.

The apparatus further includes a closure means for securing the membrane disposed between the two planar members such that the aperture or apertures expose a portion of the membrane to the surrounding environment.

In the Examples, an apparatus for tissue culture that, when assembled, constitutes a bilaminar lens shaped closed pouch is described. The membrane used in the Examples is a thin transparent membrane of Type 1 collagen which is reinforced with a nylon veil cloth. The inner side of each membrane, the side facing the interior of the pouch, has a waffled configuration and the outer side incorporates a nylon veil cloth. This configuration, the waffled pattern of the interior wall of the pouch and the nylon veil cloth on its external surface, provides a membrane of great tensile strength, and yet is easily prepared for histologic cross sections with a microtome.

When culturing cells or tissues using the present apparatus, all the cells of the inoculum and their viable progeny remain in the pouch during the culture period. The microcrypts in the waffle serve as individual chambers in which cells of the inoculum can proliferate and form histotypic groups of cells. After periods in culture the pouches can be processed using routine histologic and assay procedures.

The present invention further provides methods of manufacturing the apparatus of the present invention and methods of culturing cells using this apparatus.

BRIEF DESCRIPTION OF THE DRAWINGS

FIG. 1 shows a diagrammatic representation of a preferred embodiment of the article of the invention.

FIG. 2 shows the assembly of an apparatus for use in unilaminar culture.

FIG. 3 shows the assembly of an apparatus for use in bilaminar culture.

FIG. 4 shows two types of mesh of different sizes for making a paraffin mold.

FIG. 5 shows a nylon veil cloth for reinforcing a collagen membrane.

DESCRIPTION OF THE INVENTION

Cell Culture Apparatus

Figure 6:
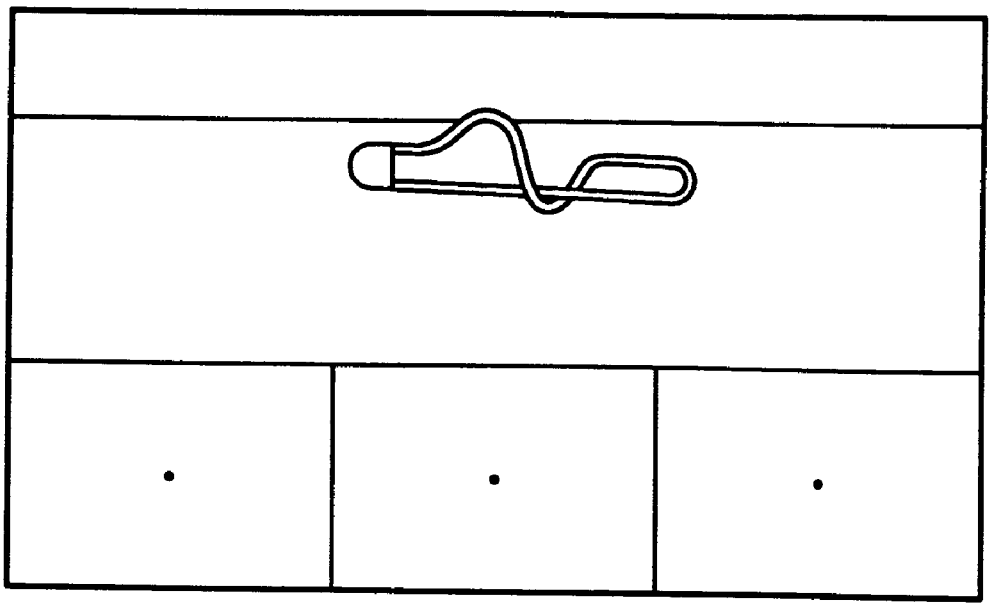
FIG. 6 shows a type of planar members.

Cells that require attachment for growth are typically cultured in an apparatus that allows the cells to form a monolayer of cells attached to the surface of the apparatus. For example, culture plates, hollow fibers and beads provide surfaces onto which cells can attach and proliferate. Cells cultured in these types of apparatuses can be difficult to process for histological analysis. Further, such apparatuses do not provide environments that allow cells to develop into three dimensional structures such as tissues. The present invention provides an apparatus for use in culturing cells and tissues that is easy to make and provides an environment in which cells form organoid three dimensional structures.

In detail, the present invention provides an apparatus for use in the culturing of cells or tissues, which comprises a pouch configured to contain cells, comprised of a membrane to which the cells are adherent. The membrane is permeable to nutrients and waste products of the cells but is impermeable to the cells. The apparatus further contains two planar members that are used to sandwich the membrane with at least one of the planar members containing an aperture so as to expose at least a portion of the membrane to the surroundings when the membrane is sandwiched between the two planar members. The apparatus further includes a closure means to secure the membrane between the two planar members.

As used herein, the pouch is defined as being comprised of two layers of membrane material, an upper layer and a lower layer. The space between the two membrane layers forms a cavity in which cells or tissues are cultured. In one embodiment, the lower layer of the membrane is further defined as having a waffle-shaped pattern of ridges or indentations on at least the surface that is contacted by the cells contained in the claimed apparatus (cavity of the pouch). In one variation, the upper layer contains a similar waffled surface, while in another embodiment, the upper layer has a smooth surface.

As used herein, a waffle-shaped pattern, or waffle-like lattice, is defined as a series of ridges or indentations on the surface of the membrane that produces individual chambers (microchambers or microcrypts) on the membrane surface. The two dimensional geometry of the chambers will depend on the positioning of the ridges or indentations on the surface. The chambers may have three or more sides. The most preferred chambers will contain from four to eight sides, preferably four sides.

The chambers formed by the waffle-shaped pattern on the membrane may be of any size. The size of the chambers formed can be varied during the manufacture of the membrane. It is preferable that the chambers formed will be from about 1 to 4 mm on each edge, preferably about 3 mm. The size will vary based on the method used to manufacture the membrane and the intended use of the apparatus/cultured cells. In the Examples, the chamber size of the collagen membrane was varied by using different mesh sizes when making the paraffin mold.

The membrane used in the present apparatus, particularly ones made up of collagen, have several advantages over a collagen coated cellulose sponge matrix. In a sponge the interstices, i.e., microchambers, vary in size, configuration, and spatial orientation. In the present apparatus, the contiguous microchambers can be of uniform size and spatial orientation providing delineated regions on the culture surface.

The pouch, as herein defined, does not need to be closed on any of the edges and can be comprised of two separate pieces of membrane material, an upper layer placed on top of a lower layer, forming a cavity between. When comprised of such separate membranes, the pouch may be sealed on one or more of the edges.

Alternatively, the pouch may be made up of a single folded membrane that then defines the upper and lower layer of membrane and the cavity between the two folded surfaces. Such a pouch may be further sealed on one or more of the edges formed when the membrane is folded.

A single membrane can also be used to form a radial gradient culture apparatus. In a radial culture apparatus, the membrane is wrapped around a cylindrical rod and is closed on the edge and on one end using a liquid collagen dispersion as a cement. The cylindrical chamber thus formed can be used for radial gradient culture studies as described below.

Any membranous material that is permeable to nutrients and waste products of cells but impermeable to cells, particularly a material that can be formed with a waffle-shaped surface configuration on at least one surface, may be used in the present apparatus. The membrane can be made up of naturally occurring materials, such as collagen, or can be made up of synthetic material such as a polymer or nylon. The preferred membrane material for use in the present apparatus is collagen.

The membrane used in the apparatus of the present invention can be comprised of one or more layers. For example, when a soft material such as collagen is used, a second layer comprised of a stronger material, such as a nylon veil cloth, may be added to one surface of the membrane. Such an additional layer can be incorporated during the manufacture of the membrane using methods known in the art.

For example, the following steps are used to form a collagen membrane containing a waffle lattice on one surface. A shallow, flat-bottomed pan containing some paraffin is placed on an electric warming table at a temperature a few degrees above the melting point of the paraffin. A piece of plastic or nylon mesh of desirable mesh size, for example, 1 to 4 mm square, is cut to fit loosely into the pan. The mesh is completely immersed in the 2 to 3 mm deep molten paraffin, and in 10 to 15 minutes the pan is transferred to a level surface at room temperature. About one hour later, when the paraffin is opaque and firm, the mesh is gently stripped away from the paraffin, leaving an impression of the mesh on the paraffin surface. A solution of collagen dispersed in methyl alcohol is poured into the pan, covering the impression in the paraffin uniformly and completely.

To strengthen the membrane, a wide mesh of nylon fabric, such as veil cloth, is moistened in methyl alcohol and placed on the collagen dispersion. After several days, with complete evaporation of the volatile solvent, the dry collagen membrane is cured in the pan by exposure overnight to 0.50% of $NH_4OH$ in methyl alcohol. The membrane is rinsed in methyl alcohol, dried, and then stripped from the paraffin template. Residual particles of paraffin adherent to the collagen are removed by immersing the membrane over night in xylene, a paraffin solvent. After drying, the membrane is rinsed in methyl alcohol and air dried. The nylon reinforced waffle collagen membrane is ready for use as a substrate for unilaminar or bilaminar culture. The collagen membrane with its waffle pattern of square indentations and nylon mesh reinforcement is strong, yet easily cut for histologic study.

A skilled artisan can readily adapt membrane forming methods so as to produce a membrane having a waffled surface.

As provided above, the apparatus of the present invention further contains two planar members that are used to sandwich the pouch formed by the membrane. The two planar members used in the present apparatus may be made of any material but it is preferred that they are comprised of an inert material that is transparent, impermeable to cells and nutrients and is both strong and resilient. The preferred material is plastic.

The two planar members may be provided as separate planar members or can be connected at one or more edges. Any configuration of two planar members can be used so long as a membrane pouch containing cells can be sandwiched between the members.

At least one of the planar members further contains an aperture. The aperture exposes at least a portion of the membrane, when sandwiched between the two planar members, to the surroundings. The exposed area forms the pouch in which cells or tissues are cultured. In one variation of the present apparatus, only one of the planar members contains an aperture. This configuration provides a unilaminar culture environment in which cells closest to the aperture are exposed to more nutrients and oxygen than cells closest to the surface without the aperture.

In another variation, both of the planar members contain apertures so as to expose two sides of the pouch to the surroundings. This configuration provides a bilaminar culture environment in which cells at both surfaces can be exposed to the same amount of nutrients and oxygen. Such a configuration can be further used to simultaneously expose cells to a nutrient medium and chemical treatment.

An example of planar members that can be used in the present apparatus is made from plastic ID covers (FIG. 6). Three sets of planar members can be prepared from a standard size cover. A typical transparent plastic culture holder is about ⅞" wide, with flaps measuring about 1 ¼" long. Two apertures, each measuring approximately 5/16" in diameter, are made with a hand punch exactly opposite each other, on each leaf of the folded plastic (FIG. 7). It is through these apertures that exchange of metabolites with the medium takes place when the system is assembled and placed in a container means.

The apparatus of the present invention further comprises a closure means for securing the membrane between the two planar members. Any closure means can be used for this purpose so long as the closure means provides pressure along at least part of the surface of the two planar members. The closure means can be part of the planar members or can be a separate component. For example, closure means which are part of the planar members can include, but are not limited to, tabs and folds of plastic. Examples of separate closure means include, but are not limited to, cotter pins, clips, and clamps. It will readily be appreciated that the number and positioning of the closure means will depend upon the type of planar members employed. A skilled artisan can readily apply any closure means technology to the apparatus of the present invention. In the examples that follow, a stainless steel cotter pin is used as a closure means.

The apparatus of the present invention may further contain a container means for use in culturing cells using the present apparatus. Any container means into which the apparatus of the present invention can be placed can be used. The preferred container means will be sterilizable, will be able to hold a medium, preferably a liquid medium, and will be easy to manipulate.

Use of the Apparatus of the Present Invention

The apparatus of the present invention provides advantages over presently art-known apparatuses in its flexibility of culture environments. For example, using planar members that contain a single aperture, a gradient culture environment in which the chamber wall adjacent to the perforation is relatively aerobic and the opposite wall relatively anaerobic will be provided. By incubating cells in an apparatus containing two apertures, a bilaminar chamber that allows diffusion of metabolites and gasses across both sides of the chamber is created. Both configurations allow cells to form three dimensional structures.

The apparatus of the present invention can be used in a variety of tissue or cell culture settings and for a variety of uses. The apparatus provides a setting where inocula of tissues or cells of various kinds, such as skin cells, established cell lines, or fragments of freshly removed tissue, can be cultivated under conditions where cells are contained in proximity to one another throughout culture periods of many days, and where there are available surfaces suitable for cell attachment, migration, proliferation, and histotypic association.

Prior to use, the components of the apparatus of the present invention (the planar members, the cotter pin, and the membrane) are sterilized, preferably by immersion in methyl alcohol for 3 hours, then air dried. An inoculum is applied to a piece of membrane after the area of the membrane is moistened with an adhesive gel (the cells are inoculated on the waffled surface if such a membrane is used). The membrane is then folded, or a second membrane applied on top. The membrane(s) is then inserted between the planar members, and the apparatus secured with a closure means. The apparatus is placed into a container means containing growth medium or assay reagent. This provides a pouch-shaped chamber containing or lined by a membrane, with surfaces of the membrane exposed to the medium or reagent in the container through the aperture in the plastic holder. When cells or tissues grow within the apparatus, the chamber bulges to form a lenticular shape.

Any cell or tissue explant can be cultured in the apparatus of the present invention. Preferred cells for culture in the present apparatus are cells that require attachment and cell-to-cell contact for growth. Such cells include, but are not limited to, eukaryotic cells such as mammalian cells.

In addition to cells, cell masses or tissue explants can be cultured in the present apparatus. Cells, cell masses and tissue explants can be primary explants, being derived directly from a patient or organism, or can be cells or tissues that have been maintained in culture for an extended period of time.

The cells, or inoculum, can be inoculated directly to the surface of the membrane prior to assembly of the apparatus. Alternatively, a biological adhesive gel, such as Matrigel™, egg white, or chicken plasma clot, can be used to cement the cells to the membrane surface. A skilled artisan can readily employ such biological adhesive gels as needed.

The apparatus of the present invention is intended for use in culturing cells. Such culturing can be for short periods of time, from several minutes to several hours, or can be for prolonged periods of time and may involve many cycles of cell division. The period of time the apparatus is used for culturing will vary depending on the need and use to which the apparatus is put.

When cells are cultured using the apparatus of the present invention, the aperture in at least one of the planar members is in contact with a culture medium or solution used in an assay. When the apparatus is used to culture cells through one or more cycles of cell division, the aperture is bathed by a medium, such as a liquid medium, for example by placing the apparatus in a dish or tube containing a liquid medium. The dish or tube can further be agitated by using a rocker-type platform or gyratory-type shaker. A skilled artisan can readily adapt a variety of culture media types and conditions for use with the apparatus of the present invention.

When the apparatus of the present invention is used for culturing cells during assays, the apparatus may be contacted with one or more solutions used in the assay, for example, labeling media or diagnostic and assay reagents. Because of the flexibility provided by the apparatus of the present invention, the apparatus can be used for a wide variety of assay purposes. For example, effects of a histophysiologic gradient on the architecture of growth and differentiation can be recognized on histologic section in a populated cavity within the present apparatus.

The apparatus of the present invention is particularly useful for culturing cells that form histotypic arrangements in culture. Such cells must occur in dense populations with limits to their free migration.

The histology of skin serves as an example. The epidermis consists of many layers of stratified epithelium. The superficial layers near the free surface are mature, keratinized. The basal zone, farthest from the surface, is proliferative, and the balance of basal renewal and superficial desquamation operates in a regulated way through the life of the individual. Nutrients for the epithelium diffuse from the supporting stroma across an interface to the basal epithelium. Products of metabolism from the epithelium are passed in the opposite direction across the interface to the stroma.

In the present apparatus, the collagen membrane is a surrogate for the stromal-epithelial interface. All metabolites for the cultured cells diffuse from the pool of medium across the interface. Metabolic products of the cells diffuse in the opposite direction and drain into the nutrient pool. Coincidentally, there is a gradient of maturation of cells from the basal surface, attached to the substrate, to the free surface of the epithelium. Furthermore epithelial inocula, as they proliferate and migrate, become a lining of cells that is continuous. Here, as in vivo, there are no epithelial sheets with stable free edges.

There are many configurations for using the present apparatus for organoid or histophysiological gradient growth. When a waffled membrane is seeded lightly with a suspension of tumor cells, the degree and type of genetic heterogeneity of the tumor can be studied. Cells adherent to the membrane surface can be cemented in place with a biologic adhesive gel. Cells, attached to the closed side of each microchamber of the waffle, engage in exchange of metabolites by diffusion with the pool of medium across the outer smooth surface of the membrane. Larger explants of tissue can also be cemented to the waffle surface.

In another configuration, a radial gradient culture apparatus, a waffle membrane made into a cylindrical culture chamber can be used in several ways, including study of fragments of individual patients'tumors. In each closed cylindrical culture chamber some of the large molecular products of synthesis by the inoculum may be retained. The fragment encased in the chamber can give rise to organized tissue as cells attach, migrate, and proliferate along the axis of the cylinder.

Of significance too is the potential use of the present apparatus in studies of transformation, carcinogenesis, and aging (Leighton, J., *In Vitro Cell. Dev. Biol.* (1991) 27A:786–790; Leighton, J., *In Vitro Cell. Dev. Biol.* (1992) 28A:482–492). Normal young adult rat bladder cells, seeded as tissue explants, give rise to a lining of rat bladder urothelium in a pattern of diffuse hyperplasia after two weeks in culture, and of nodular hyperplasia after two months. A carcinogenic stimulus, physical or chemical, applied for a defined time period to one segment of the exterior of the chamber, may be expected to induce nodular hyperplasia in a shorter time than in the adjacent non-treated lining cells.

In the present closed pouch culture apparatus, a new instrument for studying the structural dynamics of tissue formation and function is provided. Potential areas of study include developmental biology, cellular ecology, aging, virology, and cancer. Certain categories of problems passed over previously because of inadequate instruments can now be considered for study. Basic problems of proliferation, stratification, polarization, and interaction of cells in tissues can be explored under relatively controlled conditions of physical and chemical environment.

The apparatus of the present invention provides an ideal format for simultaneously testing a variety of agents in a uniform yet separated culture environment. For example, therapeutic agents or assay components can be directly injected into individual pouches containing growing cells, the effects of which can then be determined. For example, tumor cells can be removed from a patient and grown in the apparatus of the present invention, and various therapeutic modalities can be tested on individual pouches to determine the most effective method of suppressing, modulating or destroying the tumor tissue.

An area of clinical importance is the stability/instability of interepithelial tissue boundaries. Some of these zones are well known clinically, such as the transformation zone separating the endocervix and vaginal cervix where pre-invasive carcinoma of the cervix often originates. The abnormal epithelium often spreads to replace large patches of normal epithelium before it invades the wall of the cervix. Another example is the poorly understood pattern of intraepithelial invasion seen in Paget's disease of the breast. Models can be readily developed using the pouch apparatus of the present invention that reconstitute both stable and unstable interepithelial tissue boundaries that can then be manipulated experimentally.

Kit Containing the Apparatus of the Present Invention

The present invention further provides kits comprising the components of the apparatus of the present invention. Specifically, the kits of the present invention comprise 1) one or more membranes that are permeable to nutrients and waste products of cells but impermeable to cells, 2) two planar members, at least one of the planar members containing an aperture, and 3) a closure means. The kit may further comprise a biological adhesive gel, such as Matrigellm or plasma clot, a container means to contain the apparatus, and culture media. Each of the various configurations of the membrane, i.e., one or more waffled surfaces, one membrane that can be folded or two separate membranes and the presence of a support layer; the planar members, i.e., a single planar member which can be folded, two separate planar members and apertures in one or both planar members; and the closure means, are described in detail above. A skilled artisan can readily package the components of the apparatus of the present invention in a kit format for use by a skilled artisan.

The following examples are intended to illustrate but not to limit the invention.

EXAMPLE 1

Collagen Dispersion

The collagen dispersion used to make the collagen membranes was provided by Dr. Richard L. Kronenthal, Ethicon Division, Johnson & Johnson, Somerville, N.J. It is prepared from the deep flexor tendon of cattle. The final product contains about 1% collagen in fibrillary form, dispensed in a methanol water base containing 2%. cyanoacetic acid (Leighton, J., et al., *Science* (1967) 155:1259–1261).

Chicken Plasma Clot

In earlier histophysiologic gradient cultures, a chicken plasma clot served as the adhesive for cementing fragments of tissues to the collagen membrane. The cementing gel was prepared by combining small volumes of heparinized chicken plasma and of chick embryo extract. The Harlan Co. of Indianapolis provides heparinized chicken plasma. Chick embryo extract can be prepared by a skilled artisan using a variety of art known.

Inocula

Inocula that have been used in refining the apparatus include pieces of tissue from the 10 to 12 day old chick embryo, including skin, trachea, and intestine, several human mammary cancer cell lines, dog kidney cell line MDCK, and rat bladder carcinoma NBT-II.

Waffle Membrane

An aliquot of collagen dispersion is converted to a thin transparent waffle membrane by diluting it 1:1 or 1:2 in methyl alcohol and pouring it onto a paraffin surface, which has been prepared for the overlay of collagen dispersion using the following steps.

The paraffin, about 3 mm thick, rests in a flat rectangular pan on a histology hot plate and is completely melted. A rectangle of 3 mm square plastic mesh, measuring almost the area of the pan, is placed on the molten paraffin, and submerged. In a few minutes the pan is transferred to a level table at room temperature. In 15 minutes, after the paraffin has fully hardened, the nylon mesh is stripped from the paraffin, leaving behind a waffled impression that serves as the template for the collagen dispersion.

Two types of nylon cloth are used for different purposes. FIG. 4 shows two examples of mesh, one of plastic, the other of nylon, exact size, that can provide the template for the waffle as just described. FIG. 5 shows a nylon veil cloth, exact size, that is used to increase the resilience of the collagen waffle membrane. It is added to the collagen dispersion moments after the dispersion has been placed on the paraffin surface that bears the waffle impression. After the dispersion medium has evaporated, and dilute $NH_4OH$ used to cure the membrane, the membrane is dried and then easily stripped intact from the paraffin surface, presenting a fine waffled surface on one side, with an intrinsic reinforcement by the veil cloth on the other side.

Unilaminar Apparatus

An inoculum is cemented with a biological adhesive gel to the waffle surface of a 3×3 cm square of membrane. The membrane is folded and inserted into a cut badge holder containing an aperture on one surface. The apparatus is secured with a cotter pin and placed into a culture tube containing media. The tube is stoppered and incubated on a roller drum or rocker platform. This is a simple inexpensive model of a unilaminar histophysiologic gradient culture (FIG. 2). Observation of the living culture can be made using an inverted microscope. After fixation, histologic sections are prepared through the most densely cellular part of the culture.

Bilaminar Cultures

An inoculum is cemented with a biological adhesive gel to the waffle surface of a 3×3 cm square of membrane. The membrane is folded and inserted into a cut badge holder containing an aperture on both surfaces. The apparatus is secured with a cotter pin and placed into a culture tube containing medium. The tube is stoppered and incubated on a roller drum or rocker platform. This is a simple inexpensive model of a bilaminar histophysiologic gradient culture (FIG. 3). Observation of the living culture can be made using an inverted microscope. After fixation, histologic sections are prepared through the most densely cellular part of the culture.

Radial Gradient Cultures

The culture chamber here is prepared by taking a 3 cm square of waffle membrane, wrapping the waffle side around a plastic rod 2 mm in diameter, and closing the cylindrical chamber produced, using as a cement one or two drops of a collagen dispersion. During the drying process, the cemented surfaces are clamped with a hemostat to keep the contacting surfaces tightly together. Then one end of the collagen chamber is also closed with collagen cement using a hemostat. After the collagen cement dries a second process of curing with dilute $NH_4OH$ follows, with subsequent washing. An earlier procedure for preparing a collagen membrane, intrinsically reinforced with nylon veil cloth, has been described. (Leighton, J., *In Vitro Cell. Dev. Biol.* (1992) 28A:482–492).

Inoculation of Cells in a Radial Culture Apparatus

A segment of colored plastic tube is inserted in the culture chamber, and extends just beyond the opening of the chamber. A small plastic pipette containing the inoculum is inserted in the colored tube. The inoculum is expressed into the culture chamber near its sealed end, and the pipette tip removed. The plastic tube is also removed from the chamber. There is no contamination of the lining of the chamber by residues of the inoculum as the pipette is removed. The open end of the chamber is then closed with a ligature.

I claim:

1. An apparatus for use in culturing cells comprising:
   one or two membranes that are permeable to nutrients and waste products of said cells but impermeable to said cells and one or two planar members that are impermeable to said nutrients and waste products wherein when only one membrane and/or planar member is present, two opposing surfaces are created by folding the membrane and/or planar member over onto itself;

said membrane or membranes disposed on opposing surfaces of said planar member or members so as to form a sandwich between a first planar member layer, one layer of membrane, a second layer of membrane and a second planar member layer, wherein at least one planar member layer contains an aperture so as to expose a portion of at least one layer of the membrane to the surroundings when said two layers of membrane are sandwiched between the two planar member layers; and a closure means to secure the membrane layers between the two planar member layers.

2. The apparatus of claim 1 wherein both planar member layers contain an aperture, and wherein said apertures are in corresponding positions in each of the two planar member layers.

3. The apparatus of claim 1 wherein the membrane is a collagen membrane.

4. The apparatus of claim 3 wherein the collagen membrane is reinforced with a cloth mesh.

5. The apparatus of claim 1 wherein said membrane has a waffled pattern on at least one surface.

6. The apparatus of claim 1, wherein said membrane is a single collagen membrane and said membrane is folded to create said two layers of membrane that are sandwiched between said planar members.

7. The apparatus of claim 1 wherein the planar member layers are constructed of transparent plastic.

8. The apparatus of claim 1 wherein the closure means is a cotter pin.

9. The apparatus of claim 1 which further contains cells.

10. The apparatus of claim 9, wherein said cells are comprised of adherent cells.

11. An improved method for culturing cells, said improvement comprising culturing cells with the apparatus of claim 1.

12. The apparatus of claim 1 wherein the planar member layers are forned from a single planar member and said planar member is folded so as to create said two layers of planar member that sandwich said membrane layers.

* * * * *